United States Patent [19]

Ueda et al.

[11] Patent Number: 4,730,061
[45] Date of Patent: Mar. 8, 1988

[54] PYRONE-3-CARBOXAMIDE COMPOUNDS

[75] Inventors: Yoichiro Ueda; Yukihisa Goto; Kazuhisa Masamoto, all of Himeji; Yoshiyuki Hirako, Otake; Hiroshi Yagihara, Himeji; Yasuo Morishima, Kobe; Hirokazu Osabe, Himeji, all of Japan

[73] Assignee: Daicel Chemical Industries Ltd., Osaka, Japan

[21] Appl. No.: 815,229

[22] Filed: Dec. 31, 1985

[30] Foreign Application Priority Data

Dec. 29, 1984 [JP] Japan .................. 59-278974

[51] Int. Cl.$^4$ .......................... C07D 309/22
[52] U.S. Cl. ................................ 549/419
[58] Field of Search .......................... 549/419

[56] References Cited

U.S. PATENT DOCUMENTS 4,060,533 11/1977 Nadel .................. 549/419

FOREIGN PATENT DOCUMENTS 45-31663 10/1970 Japan .

OTHER PUBLICATIONS

Ozaki, Chem. Abstr., 74, 53811z (1971) (Abstract of Japan 70-31,663).

*Primary Examiner*—Nicky Chan
*Attorney, Agent, or Firm*—Stiefel, Gross, Kurland & Pavane

[57] ABSTRACT

A pyrone-3-carboxamide compound of the formula (I):

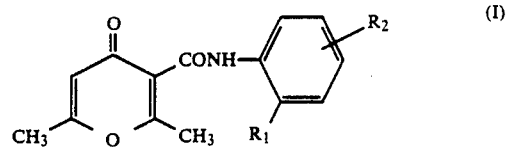

in which $R_1$ is an alkyl group, and $R_2$ is an alkyl group or a halogen atom, which is useful as a medicine and an agricultural chemical or an intermediate thereof.

5 Claims, No Drawings

PYRONE-3-CARBOXAMIDE COMPOUNDS

BACKGROUND OF THE INVENTION

1. Field of the Invention

This invention relates to novel compounds which belong to pyrone-3-carboxamide compounds, particularly 2,6-dimethyl-4-oxo-4H-pyran-3-carboxamides. The compounds of this invention show a growth inhibitory activity on plants and also are useful as intermediates for preparing medicines or agricultural chemicals.

2. Description of the Prior Art

Certain compounds belonging to 2,6-dimethyl-4-oxo-4H-pyran-3-carboxamides have been mentioned in the literature.

That is, it has been known that the treatment of o-haloacetoanilides (2-chloro, 2-bromo, 2,4-dichloro or 2,5-dichloro compounds) with polyphosphoric acid for an hour at 140° C. gave the corresponding halogen derivatives of 2,6-dimethyl-4-oxo-N-phenyl-4H-pyran-3-carboxamide (A. K. Mallams & S. S. Islaelstam: J. Org. Chem., 29, 3548(1964); A. K. Mallams: J. Org. Chem., 29, 3555(1964). This method using polyphosphoric acid was applied to other acetoacetoanilides (2-fluoro, 2-piperidino, 2-hexahydroazepinyl, 2-morpholino, 2-pyrrolidinyl or the like) to yield the corresponding 2,6-dimethyl-4-oxo-4H-pyran-3-carboxamide compounds [R. Garner & H. Suschitzky: J. Chem. Soc. (C), 186(1966)].

The formation of 2,6-dimethyl-N-(4-nitrophenyl)-4-oxo-4H-pyran-3-carboxamide was identified as the reaction product of p-nitroaniline and diketene [Kato & Kubota: Yakugakuzassi, 87, 1212(1967)]. Also, N-(2-chlorophenyl)-2,6-dimethyl-4-oxo-4H-pyran-3-carboxamide was obtained by treating 2,6-dimethyl-4-oxo-4H-pyran-3-carboxylic acid with thionyl chloride followed by the reaction with o-chloroaniline, or heating the p-nitrophenyl ester of 2,6-dimethyl-4-oxo-4H-pyran-3-carboxylic acid and o-chloroaniline for 4.3 hours at 110° C. [Toda: Yakugakuzassi, 87, 1351(1967)]. This reference discloses pyrone-3-carboxamide compounds which were obtained by the reaction of 4-aminotropolones with diketene.

Also, Japanese Patent Publication No. 45(1970)-31663 discloses a process for preparing 2,6-dimethyl-4-oxo-4H-pyran-3-carboxamides which comprises reacting isocyanates and diketene in the presence of an acid catalyst. In the examples this publication describes 2,6-dimethyl-4-oxo-N-phenyl-4H-pyran-3-carboxamide, 2,6-dimethyl-N-(2-methylphenyl)-4-oxo-4H-pyran-3-carboxamide, N-(2-chlorophenyl)-2,6-dimethyl-4-oxo-4H-pyran-3-carboxamide, 2,6-dimethyl-N-(2-nitrophenyl)-4-oxo-4H-pyran-3-carboxamide, N-(2,5-dichlorophenyl)-2,6-dimethyl-4-oxo-4H-pyran-3-carboxamide, oxo-4H-2,6-dimethyl-N-(3-nitrophenyl)-4-oxo-4H-pyran-3-carboxamide and 2,6-dimethyl-N-(4-methylphenyl)-4-oxo-4H-pyran-3-carboxamide.

Further, 2,6-dimethyl-4-oxo-N-phenyl-4H-pyran-3-carboxamide, N-(4-methoxyphenyl)-2,6-dimethyl-4-oxo-4H-pyran-3-carboxamide and N-(4-chlorophenyl)-2,6-dimethyl-4-oxo-4H-pyran-3-carboxamide have been disclosed as the reaction products of 3-morpholinocrotonanilide compounds and diketene [Kato et al: Yakugakuzassi, 101, 43(1981)].

There have also been references to pyrone-3-carboxamide compounds which correspond to aminotropones (H. Toda & S. Seto: Chem. Pharm. Bull., 19, 1477(1971), aminopyridines (T. Kato et al: Chem. Pharm. Bull., 20, 133(1972); ibid. 28, 2129(1980); H. L. Yale et al: J. Heterocyclic Chem., 14, 637(1977) and 2-amino-1,3,4-thiadiazoles (R. F. Lauer et al: J. Heterocyclic Chem., 13, 291(1976), respectively.

The above mentioned Japanese Patent Publication No. 45(1970)-31663 discloses that 2,6-dimethyl-4-oxo-4H-pyran-3-carboxamides have utility as agricultural drugs such as control agents of sheath blight of rice, nematocides, or acaricides, or drugs such as antiviral agents or the like, but does not disclose any data supporting such utility.

As discussed above, there were no reports on the pyrone-3-carboxamide compounds represented by formula (I) of the present invention, together with no suggestion on their plant growth inhibitory activity.

SUMMARY OF THE INVENTION

This invention is directed to compounds of the formula (I) and salts thereof,

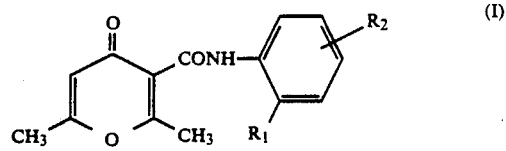

wherein, $R_1$ is an alkyl group and $R_2$ is an alkyl group or halogen atom.

DESCRIPTION OF PREFERRED EMBODIMENTS

The term "alkyl group" in this invention means those alkyl groups containing preferably 1-5 carbon atoms. Also, "halogen atom" in the symbol $R_2$ means desirably fluorine, chlorine or bromine atom.

In $R_1$ and $R_2$, the preferred examples of alkyl groups are methyl, ethyl or isopropyl, and that of the halogen atom is chlorine.

The compounds of formula (I) of this invention may be generally prepared with good yield by reacting a butyrylanilide derivative of the formula (II):

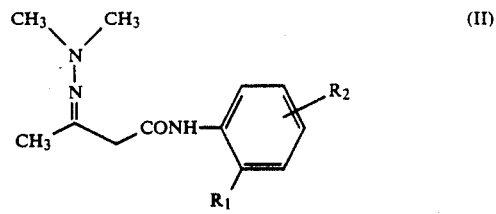

in which $R_1$ and $R_2$ are the same as those in the formula (I), with diketene or its addition product with acetone, i.e., 2,2,6-trimethyl-4H-1,3-dioxin-4-one.

The butyrylanilide derivative of the formula (II) can be easily prepared by reacting the corresponding acetoacetanilide derivative with N,N-dimethylhydrazine under a dehydro-condensation condition in accordance with conventional methods. The intermediate of the formula (II) is desirably used after isolation and purification but may be directly used as the reaction mixture mentioned above.

The reaction of the compound of the formula (II) with diketene or 2,2,6-trimethyl-4H-1,3-dioxin-4-one is conducted in an appropriate solvent under heating. The solvents desirably provide less solubility for the object compounds at cooler temperatures. Aromatic hydrocarbons such as benzene, toluene, xylene and the like are advantageously used as such solvents. The reaction temperature is in the range from about 60° C. to about 130° C. in the case of use of diketene and in the range from 100° C. to 140° C. in case of 2,2,6-trimethyl-4H-1,3-dioxin-4-one.

This invention is illustrated further by examples. Also, growth-inhibitory activities on plants of the compounds of the invention are shown in reference examples.

Furthermore, related specific compounds in addition to the compounds shown in the examples are as follows;
N-(3-chloro-2-methylphenyl)-2,6-dimethyl-4-oxo-4H-pyran 3-carboxamide,
2,6-dimethyl-N-(2,4-dimethylphenyl)-4-oxo-4H-pyran 3-carboxamide,
2,6-dimethyl-N-(2,5-dimethylphenyl)-4-oxo-4H-pyran 3-carboxamide.

EXAMPLE 1

N-(2,6-Diethylphenyl)-2,6-dimethyl-4-oxo-4H-pyran carboxamide

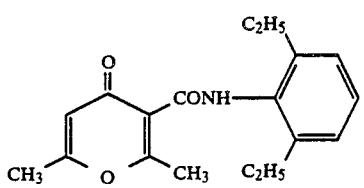

A mixture of 25.0 g (90.8 m mol) of N-(2,6-diethylphenyl)-3-(N,N-dimethylhydrazono)butyrylamide (mp 107°-108.5° C., recrystallized from hexane) and 130 ml of toluene was refluxed, to which a solution of 28.4 g (200 m mol) of 2,2,6-trimethyl-4H-1,3-dioxin-4-one in 70 ml of toluene was added dropwise over a period of 30 minutes. The mixture was further refluxed for 2 hours. After distilling off the solvent, 200 ml of ethyl ether was added to the residue. The mixture was well mixed and filtered to remove insoluble material. The filtrate was concentrated to obtain a residue. The residue was subjected to chromatography to remove highly polar impurities. The resultant product was recrystallized from hexane to obtain 20.2 g (yield 74%) of the title compound. The physical properties of the compound are referred to in Table 1. Numbers in the column "Evaluation" in Table 1 were obtained as follows.

A carrier was prepared by mixing 50 parts (by weight) of talc, 25 parts of bentonite, 2 parts of Solpole -9047 (Toho Chemical Co., Ltd, Japan) and 3 parts of Solpole -5039 (Toho Chemical Co., Ltd, Japan). 50 parts of a test compound and 200 parts of the carrier were mixed to obtain 20% wettable powder, followed by dispersing the powder in distilled water to make a dispersion of the definite concentrations.

Seeds of Oryza sativa L., Echinochloa crus-galli L., and Raphanus sativus L. were germinated in a laboratory dish, to which the dispersion was added. After breeding for 7 days in a thermostatic box kept at 25° C. under fluorescent illumination, plant growth was observed. In the column "Evaluation" of Table 1, the designation 1 denotes no influence, 2 denotes 25% growth inhibition, 3 denotes 50% growth inhibition, 4 denotes 75% growth inhibition and 5 denotes 100% growth inhibition.

EXAMPLE 2

N-(2,3-Dimethylphenyl)-2,6-dimethyl-4-oxo-4H-pyran-3-carboxamide

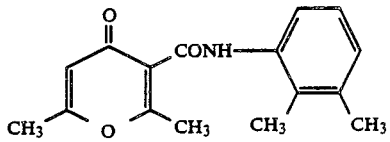

A mixture of 10.3 g (50 m mol) of N-(2,3-dimethylphenyl)-3-oxo-butanamide, 4.50 g (75 m mol) of N,N-dimethylhydrazine and 60 ml of toluene was stirred for 8 hours at 60° C. Then, unreacted N,N-dimethylhydrazine and the resulting water together with about 10 ml of toluene were distilled off outside the reaction system. 10.5 g (125 m mol) of diketene was added dropwise to the remaining solution over a period of 5 minutes, while refluxing. The mixture was further refluxed for 2 hours and cooled to room temperature. The resulting crystals were filtered, washed and dried to obtain 8.63 g (yield 64%) of the title compound.

EXAMPLE 3

N-(2-Chloro-6-methylphenyl)-2,6-dimethyl-4-oxo-4H-pyran-3-carboxamide

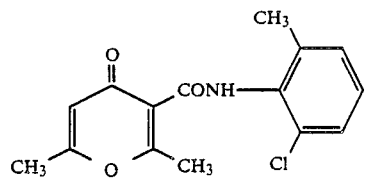

The title compound was prepared from N-(2-chloro-6-methylphenyl)-3-oxo-butanamide and N,N-dimethylhydrazine as the raw materials in a similar manner to the method described in Example 2. (Yield: 45%).

EXAMPLE 4

N-(2,6-dimethylphenyl)-2,6-dimethyl-4-oxo-4H-pyran-3-carboxamide

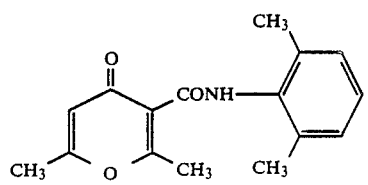

The title compound was prepared from N-(2,6-dimethylphenyl)-3-oxo-butanamide and N,N-dimethylhydrazine as the raw materials in a similar manner to the method described in Example 2. (Yield: 63%).

EXAMPLE 5

N-(2-Ethyl-6-methylphenyl)-2,6-dimethyl-4-oxo-4H-pyran-3-carboxamide

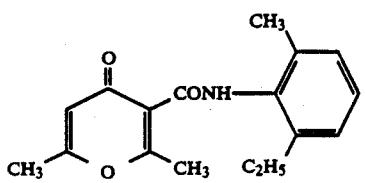

The title compound was prepared from N-(2-ethyl-6-methylphenyl)-3-oxo-butanamide and N,N-dimethylhydrazine in a manner similar to the method described in Example 2. (Yield: 58%).

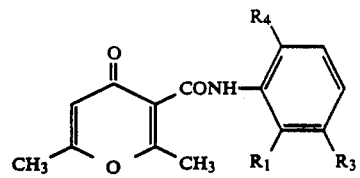

wherein R1 is an alkyl group; and one of R3 and R4 is an alkyl group or a halogen atom and the other is a hydrogen atom.

2. The compound of claim 1 in which the alkyl group has one to five carbon atoms.

3. The compound of claim 1 in which the halogen atom is a fluorine, chlorine or bromine atom.

4. The compound of claim 1 in which the alkyl group is a methyl, ethyl or isopropyl group.

5. The compound of claim 1 in which the halogen atom is a chlorine atom.

TABLE 1

| Example No. | Substituent $R_1$, $R_2$ | NMR(CDCl$_3$) δ value | | | | IR(cm$^{-1}$) $\nu_{C=O}$ (KBr) | MP (°C.) | Evaluation | | | |
|---|---|---|---|---|---|---|---|---|---|---|---|
| | | CH$_3$ at 2,6-position | H at 5 position | NH | Substituent on phenyl group | | | Con. (ppm) | Plants X | Y | Z |
| 1 | 2-C$_2$H$_5$ | 2.80 (s) | 6.24 (s) | 11.00 | 1.17 (t, 6H) | 1655 | 83.5–84.5 | 20 | 1 | 2 | 3 |
| | 6-C$_2$H$_5$ | 2.29 (s) | | | 2.61 (q, 4H) | 1675 | | 100 | 2 | 4 | 4 |
| 2 | 2-CH$_3$ | 2.83 (s) | 6.23 (s) | 11.66 | 2.28 (s, 6H) | 1645 | 174.5–175.5 | 20 | 1 | 1 | 3 |
| | 3-CH$_3$ | 2.28 (s) | | | | 1675 | | 100 | 1 | 2 | 4 |
| 3 | 2-Cl | 2.80 (s) | 6.24 (s) | 11.40 | 2.28 (s, 3H) | 1655 | 145.0–148.0 | 20 | 1 | 1 | 2 |
| | 6-CH$_3$ | 2.28 (s) | | | | 1678 | | 100 | 1 | 2 | 4 |
| 4 | 2-CH$_3$ | 2.79 (s) | 6.22 (s) | 11.18 | 2.24 (s, 6H) | 1650 | 111.5–112.0 | 20 | 1 | 1 | 1 |
| | 6-CH$_3$ | 2.28 (s) | | | | 1678 | | 100 | 1 | 1 | 3 |
| 5 | 2-C$_2$H$_5$ | 2.80 (s) | 6.23 (s) | 10.97 | 1.18 (t, 3H) | 1653 | 57.0–58.5 | 20 | 1 | 4 | 1 |
| | 6-CH$_3$ | 2.28 (s) | | | 2.24 (s, 3H) | 1683 | | 100 | 1 | 1 | 1 |
| | | | | | 2.63 (q, 2H) | | | | | | |
| Example | 2,6-dimethyl-4-oxo-N—phenyl-4H—pyran-3-carboxamide (known compound) | | | | | | | 20 | 1 | 1 | 1 |
| | | | | | | | | 100 | 1 | 1 | 1 |

X: *Oryza sativa* L.
Y: *Echinochloa crus-galli* L.
Z: *Raphanus sativus* L.

We claim:

1. A pyrone-3-carboxamide compound of the formula: